(12) United States Patent
Wachtler et al.

(10) Patent No.: US 7,250,199 B2
(45) Date of Patent: *Jul. 31, 2007

(54) PHENYLCYCLOHEXANES AND A LIQUID-CRYSTALLINE MEDIUM

(75) Inventors: Andreas Wachtler, Griesheim (DE); Reinhard Hittich, Modautal (DE); Eike Poetsch, Mühltal (DE); Herbert Plach, Darmstadt (DE); David Coates, Wimborne (GB); Bernhard Rieger, Münster-Altheim (DE); Joachim Krause, Dieburg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/038,170

(22) Filed: Jan. 21, 2005

(65) Prior Publication Data

US 2005/0133763 A1 Jun. 23, 2005

Related U.S. Application Data

(60) Division of application No. 09/778,808, filed on Feb. 8, 2001, now Pat. No. 6,677,002, which is a division of application No. 08/486,228, filed on Jun. 7, 1995, now Pat. No. 6,284,154, which is a continuation of application No. 08/046,286, filed on Apr. 15, 1993, now Pat. No. 5,891,360, which is a division of application No. 07/585,165, filed as application No. PCT/EP90/01330 on Aug. 13, 1990, now abandoned.

(30) Foreign Application Priority Data

| Aug. 16, 1989 | (DE) | P 39 26 871 |
| Mar. 1, 1990 | (DE) | P 40 06 313 |
| Apr. 25, 1990 | (DE) | P 40 13 084 |
| Apr. 27, 1990 | (DE) | P 40 13 467 |
| Jul. 3, 1990 | (DE) | P 40 21 154 |

(51) Int. Cl.
*C09K 19/30* (2006.01)
*C09K 19/12* (2006.01)
*C07C 25/24* (2006.01)

(52) U.S. Cl. ............ 428/1.1; 252/299.63; 252/299.66; 570/129

(58) Field of Classification Search ................ 428/1.1; 252/299.63, 299.66; 570/129; 558/425
See application file for complete search history.

(56) References Cited

U.S. PATENT DOCUMENTS

| 4,398,803 | A | 8/1983 | Pohl et al. |
| 4,405,488 | A | 9/1983 | Sugimori et al. |
| 4,565,425 | A | 1/1986 | Petrzilka et al. |
| 4,621,901 | A | 11/1986 | Petrzilka et al. |
| 4,676,604 | A | 6/1987 | Petrzilka et al. |
| 4,709,030 | A | 11/1987 | Petrzilka et al. |
| 4,770,503 | A | * 9/1988 | Buchecker et al. ...... 252/299.5 |
| 4,784,471 | A | * 11/1988 | Wachtler et al. ............ 558/425 |
| 4,818,428 | A | 4/1989 | Scheuble et al. |
| 4,871,469 | A | 10/1989 | Reiffenrath et al. |
| 5,013,477 | A | 5/1991 | Buchecker et al. |
| 5,013,478 | A | 5/1991 | Petrzilka et al. |
| 5,021,189 | A | 6/1991 | Sawada et al. |
| 5,032,313 | A | 7/1991 | Goto et al. |
| 5,122,295 | A | 6/1992 | Weber et al. |
| 5,171,469 | A | 12/1992 | Hittich et al. |
| 5,174,921 | A | 12/1992 | Buchecker et al. |
| 5,178,790 | A | 1/1993 | Weber et al. |
| 5,185,098 | A | 2/1993 | Buchecker et al. |
| 5,204,017 | A | 4/1993 | Reiffenrath et al. |
| 5,230,826 | A | 7/1993 | Boller et al. |

(Continued)

FOREIGN PATENT DOCUMENTS

DE 3732284 4/1989

(Continued)

OTHER PUBLICATIONS

Petrzilka et al., "New Liquid Crystals: The Synthesis and Mesomorphic Properties . . . ", Mol. Cryst. Liq. Cryst., 1985, vol. 131, Previously Presented. 327-342.

(Continued)

*Primary Examiner*—Shean C. Wu
(74) *Attorney, Agent, or Firm*—Millen, White, Zelano & Branigan, P.C.

(57) ABSTRACT

Novel phenylcyclohexanes of the formula I

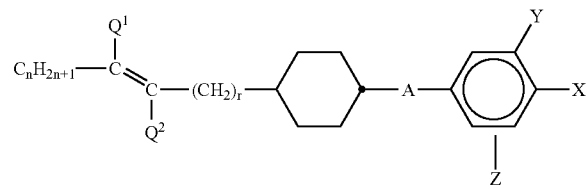

in which n is 0 to 7, $Q^1$ and $Q^2$ are H, or one of these radicals is alternatively $CH_3$, r is 0, 1, 2, 3, 4 or 5, A is trans-1,4-cyclohexylene, 1,4-phenylene, 3-fluoro-1,4-phenylene or a single bond, X is F, Cl, $—CF_3$, $—CN$, $—OCF_3$ or $—OCHF_2$, and Y and Z are each, independently of one another, H or F, with the proviso that, in the case where A is a single bond, $Q^1=Q^2=H$ and simultaneously X=CN, Y and/or Z are F.

19 Claims, No Drawings

U.S. PATENT DOCUMENTS

| | | |
|---|---|---|
| 5,230,829 A | 7/1993 | Bartmann et al. |
| 5,286,410 A | 2/1994 | Weber et al. |
| 5,286,411 A | 2/1994 | Rieger et al. |
| 5,292,452 A | 3/1994 | Buchecker et al. |
| 5,318,721 A | 6/1994 | Reiffenrath et al. |
| 5,350,535 A | 9/1994 | Rieger et al. |
| 5,368,772 A | 11/1994 | Rieger et al. |
| 5,382,379 A | 1/1995 | Onji et al. |
| 5,389,289 A | 2/1995 | Rieger et al. |
| 5,389,295 A | 2/1995 | Wachtler et al. |
| 5,397,505 A | 3/1995 | Rieger et al. |
| 5,458,805 A * | 10/1995 | Wachtler et al. ....... 252/299.63 |
| 5,807,500 A | 9/1998 | Bremer et al. |
| 5,891,360 A * | 4/1999 | Wachtler et al. ....... 252/299.63 |
| 6,143,199 A | 11/2000 | Bremer et al. |
| 6,284,154 B1 * | 9/2001 | Wachtler et al. ....... 252/299.63 |
| 6,677,002 B2 * | 1/2004 | Wachtler et al. ............ 428/1.1 |
| 6,955,837 B2 * | 10/2005 | Wachtler et al. ............ 428/1.1 |

FOREIGN PATENT DOCUMENTS

| | | |
|---|---|---|
| DE | 3906040 A1 | 9/1989 |
| EP | 205503 | 3/1989 |
| WO | WO 86/03769 A1 | 12/1985 |
| WO | WO 88/02018 A1 | 3/1988 |
| WO | WO 8801018 | 3/1998 |

OTHER PUBLICATIONS

Liquid Crystal Handbook, 1985, Previously Presented. 155-156, Original text and translation.

Pohl et al., "Multiplexible Liquid Crystalline Broad Range Systems", Mol. Cryst. Liq. Crys., 1983, Vol. 97, Previously Presented. 277-286.

* cited by examiner

PHENYLCYCLOHEXANES AND A LIQUID-CRYSTALLINE MEDIUM

This application is a divisional application of U.S. application Ser. No. 09/778,808, filed Feb. 8, 2001, which is now U.S. Pat. No. 6,677,002, which is a divisional application of divisional application no. 08/486,228, filed Jun. 7, 1995, now U.S. Pat. No. 6,284,154, which is a continuation of application No. 08/046,286, filed Apr. 15, 1993, now U.S. Pat. No. 5,891,360, which is a division of application No. 07/585,165, filed as application No. PCT/EP90/01330 on Aug. 13, 1990, now abandoned.

The invention relates to novel phenylcyclohexanes of the formula I

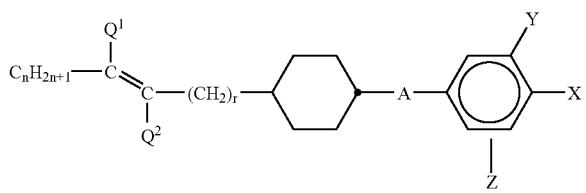

in which n is 0 to 7, $Q^1$ and $Q^2$ are H, or one of these radicals is alternatively $CH_3$, r is 0, 1, 2, 3, 4 or 5, A is trans-1,4-cyclohexylene, 1,4-phenylene, 3-fluoro-1,4-phenylene or a single bond, X is F, Cl, —$CF_3$, —CN, —$OCF_3$ or —$OCHF_2$, and Y and Z are each, independently of one another, H or F, with the proviso that, in the case where A is a single bond, $Q^1=Q^2=$H and simultaneously X=CN, Y and/or Z are F.

EP-A 0 122 389 discloses similar compounds, for example of the formula A

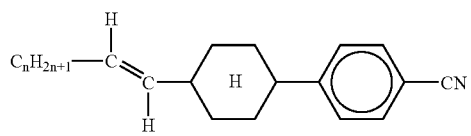

However, these compounds do not satisfy all the demands, in particular with respect to (long-term) stability, for example for use in displays having an active matrix.

German Offenlegungsschrift 29 07 332 discloses similar compounds of the formula

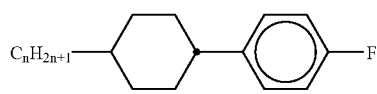

These nematogenic compounds are preeminently suitable for improving the low-temperature behavior of nematic mixtures, but, on the other hand, have relatively high values for the vapor pressure at small values of n.

EP-A 0 280 902 discloses similar compounds of the formula

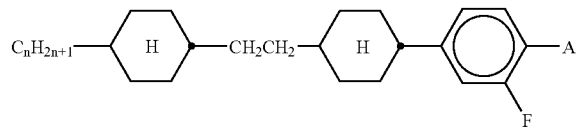

in which A is F, Cl, Br, H or CN. Although these compounds have low values for the vapor pressure, they have, on the other hand, clearly smectogenic properties. There is thus a demand for highly nematogenic compounds having low values for the vapor pressure.

In particular in displays of the supertwist type (STN) having twist angles significantly greater than 220° or in displays having an active matrix, the materials employed hitherto have disadvantages.

Like similar compounds known, for example, from German Offenlegungsschriften 26 36 684 and 29 07 332, these compounds of the formula I can be used as components of liquid-crystalline media, in particular for displays based on the principle of the twisted cell.

All the substances employed hitherto for this purpose have certain disadvantages, for example excessively high melting points, excessively low clear points, excessively low stability to the action of heat, light or electrical fields, excessively low electrical resistance, excessively high temperature dependence of the threshold voltage, and unfavorable dielectric and/or elastic properties. The invention had the object of finding novel liquid-crystalline compounds which are suitable as components of liquid-crystalline media, in particular for nematic media having a positive dielectric anisotropy, and which do not have the disadvantages of the known compounds, or only do so to a lesser extent. This object has been achieved by the provision of the novel compounds of the formula I.

It has been found that the compounds of the formula I are preeminently suitable as components of liquid-crystalline media. In particular, they can be used to obtain liquid-crystalline media having broad nematic ranges, excellent nematogeneity down to low temperatures, excellent chemical stability, pronounced $\epsilon\perp$ with a positive dielectric anisotropy, low temperature dependence of the threshold voltage and/or low optical anisotropy. In addition, the novel compounds have good solubility for other components of media of this type and a high positive dielectric anisotropy with, at the same time, favorable viscosity and excellent elastic properties. The compounds of the formula I facilitate both STN displays having a very steep electrooptical characteristic line and displays having an active matrix with excellent long-term stability.

In the pure state, the compounds of the formula I are colorless and form a liquid-crystalline mesophase in a temperature range which is favorably located for electrooptical use.

The invention thus relates to the compounds of the formula I and to the use of the compounds of the formula I as components of liquid-crystalline media, to liquid-crystalline media containing at least one compound of the formula I, and to electrooptical displays which contain media of this type.

Above and below, n, $Q^1$, $Q^2$, r, A, X, Y and Z are as defined above, unless expressly stated otherwise.

In the compounds of the formula I, the alkyl groups $C_nH_{2n+1}$ are preferably straight-chain. Accordingly, $C_nH_{2n+1}$ is preferably methyl, ethyl, n-propyl, n-butyl, n-pentyl, n-hexyl, n-heptyl or likewise preferably H. n is preferably 0, 1, 2, 3, 4 or 5.

Compounds of the formula I having branched alkyl groups may occasionally be of importance due to better solubility in the customary liquid-crystalline base materials, but in particular as chiral dopes if they are optically active. Branched groups of this type generally contain not more than one chain branch. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-heptyl (=1-methylhexyl), 2-octyl (=1-methylheptyl) and 2-ethylhexyl.

The radical

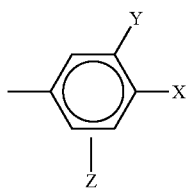

is preferably

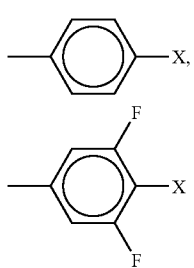

X is preferably F, Cl, —$CF_3$, $OCHF_2$ or —$OCF_3$. X is furthermore preferably CN, in particular if simultaneously Z=F and Y=F or H, in particular Y=F. Very particular preference is given to compounds where X=$CF_3$, —$OCF_3$ or —$OCHF_2$.

r is preferably 1, 2 or 3 or furthermore preferably 0. A is preferably a single bond and furthermore preferably trans-1,4-cyclohexylene or 1,4-phenylene. In the case where $Q^1=Q^2=H$, r=2 or 3, Z=H, X=F or Cl and simultaneously Y=F or H, A is preferably a single bond, 1,4-phenylene or 3-fluoro-1,4-phenylene.

In addition, the compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the reactions mentioned. Use may also be made here of variants which are known per se, but are not described in greater detail.

If desired, the starting materials can also be formed in situ, by not isolating them from the reaction mixture but instead immediately reacting them further to form the compounds of the formula I.

Preferably, an aldehyde of the formula II

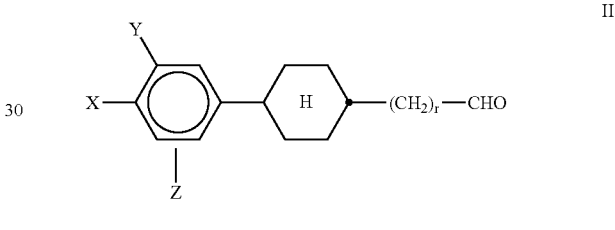

II in which X, Y and Z are as defined above, is converted into compounds of the formula I by the Wittig method using an appropriate phosphonium salt.

Some of the starting materials and the reactive derivatives thereof are known, and some can be prepared without difficulty from compounds known from the literature by standard methods of organic chemistry. For example, the precursors of the formula II which are suitable for the synthesis can be obtained by the following synthetic scheme:

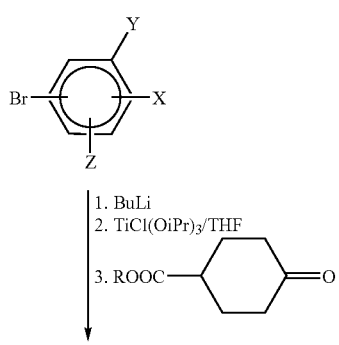

-continued
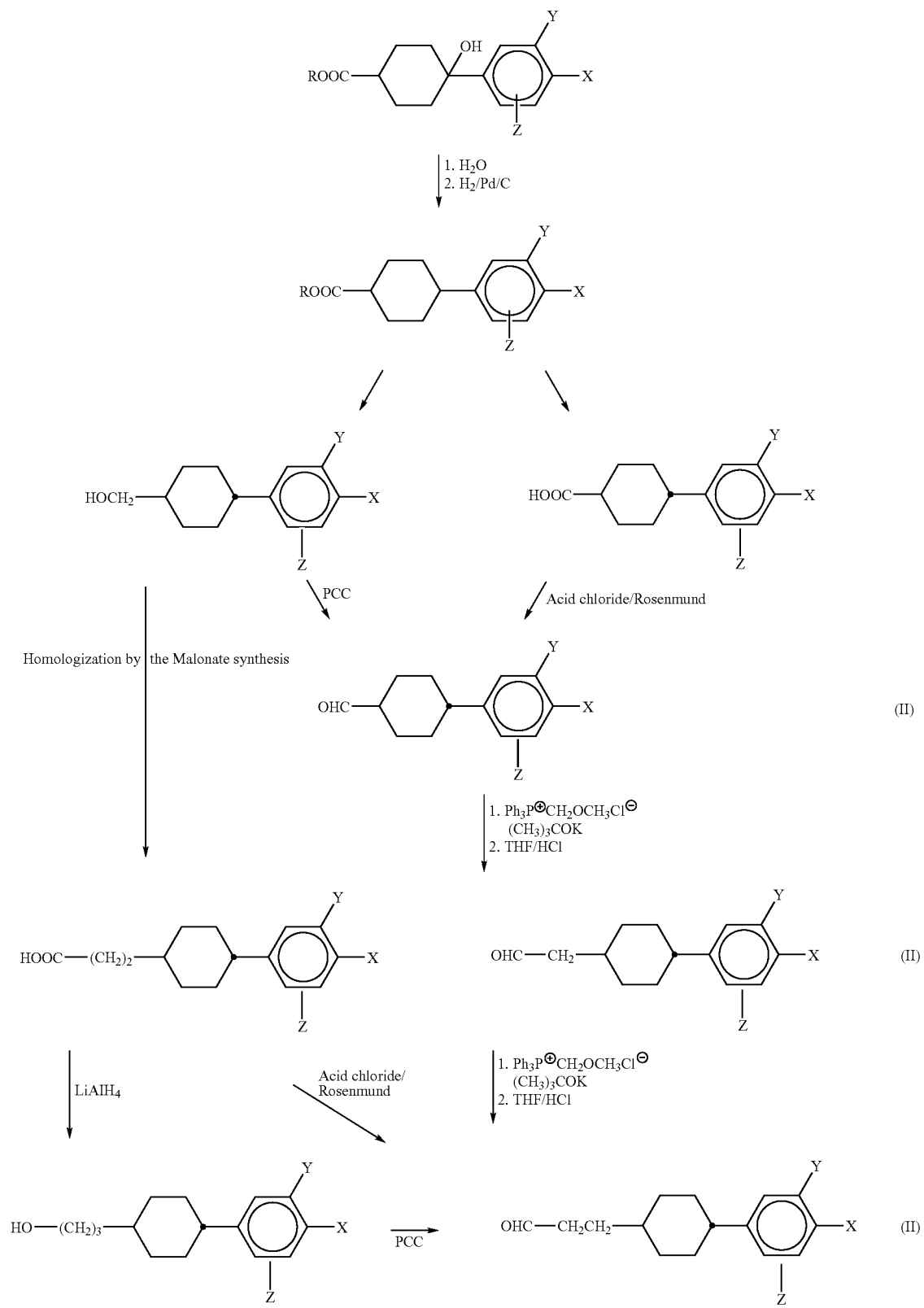

The Grignard compound obtained from the corresponding bromobenzene derivative is reacted with chlorotrialkyl orthotitanate or -zirconate by the method of WO 87/05599 to give the tertiary cyclohexanol. Elimination of water, hydrogenation of the double bond and isomerization give the trans-cyclohexanecarboxylate by customary methods. From the latter, the suitable precursors of the formula II are obtained by customary standard methods.

A possible synthesis of compounds where A=trans-1,4-cyclohexylene or 1,4-phenylene is given in the following scheme:

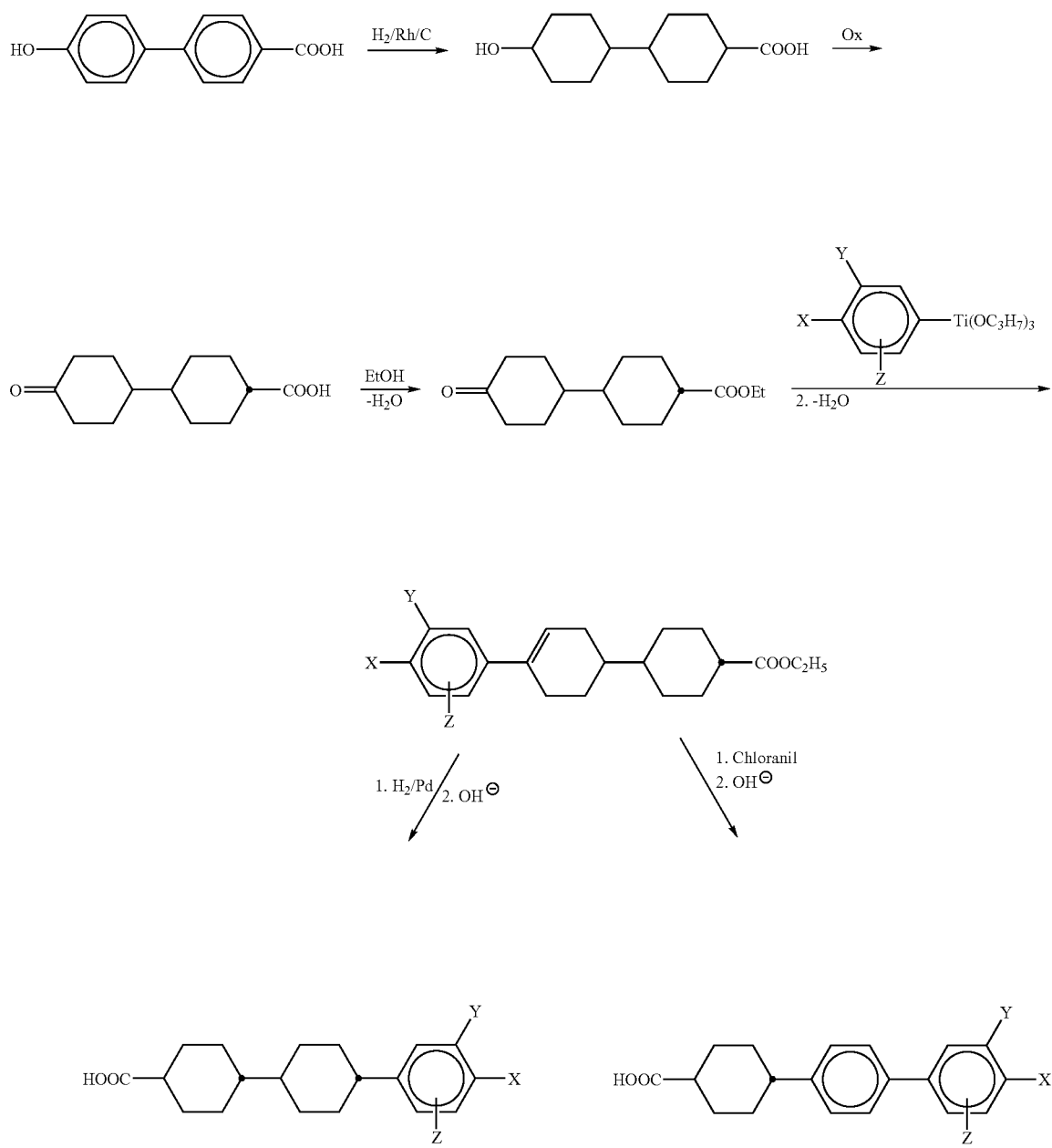

Homologization of the cyclohexanecarboxylic acids or the corresponding aldehydes gives the compounds according to the invention completely analogously to the synthesis schemes given above.

The compounds of the formula I where A=3-fluoro-1,4-phenylene are increased [sic] entirely analogously to the first synthesis scheme (preparation of compounds where A=a single bond) by using

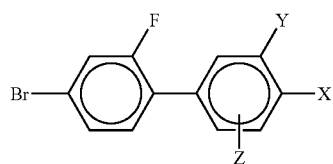

in place of the bromobenzene derivative. The bromobiphenyl compound can be prepared in a manner known per se by coupling reactions catalyzed by transition metals (E. Poetsch, Kontakte (Darmstadt) 1988 (2), p. 15).

It is obvious to a person skilled in the art that the above mentioned synthetic methods can also be modified in that the syntheses described are carried out using precursors in which the radical X is replaced by a group which can be converted into X. For example, ether cleavage of alkoxy compounds gives the corresponding phenols, from which the $OCF_3$ and $OCF_2H$ compounds can be prepared by routine methods by reaction with $CCl_4/HF$ or $CClF_2H/NaOH$. The corresponding benzoic acids can be used to prepare the nitrites or the $CF_3$ compounds by treatment with $SF_4$.

However, it often proves advantageous to react a phosphonium salt of the formula III

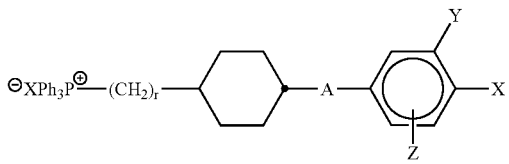

with an appropriate aldehyde by the Wittig method. The compounds of the formula III are obtained from the above-described cyclohexylmethyl alcohols by the following scheme:

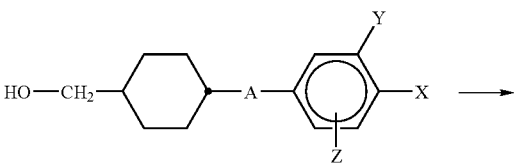

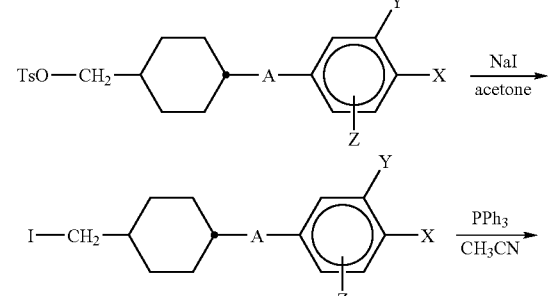

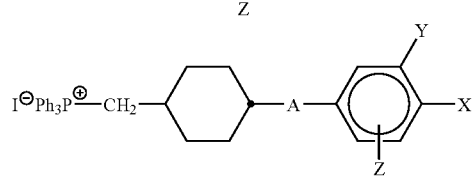

Homologization gives the corresponding higher phosphonium salts:

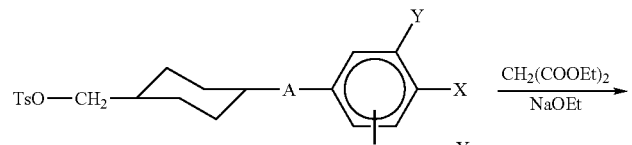

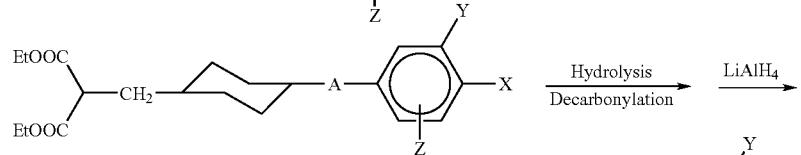

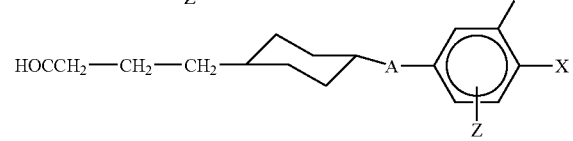

Homologization by one carbon atom is best carried out via the nitriles:

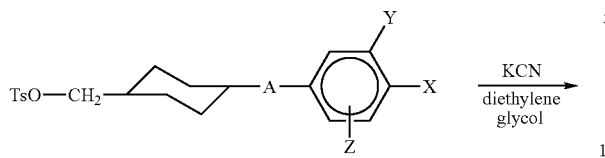

In the case of base-sensitive nitriles, the conversion to the alcohol is best carried out by reducing the nitrile to the aldehyde using DIBAH and subsequently to the alcohol using LiAlH$_4$.

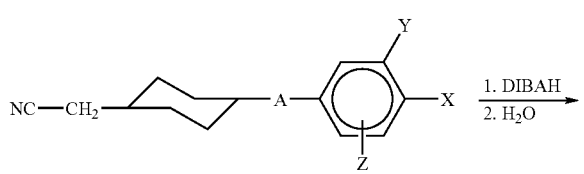

The corresponding iodides are obtained from the alcohols via the tosylates by the Finkelstein method; the iodides are then converted into the corresponding phosphonium salts by boiling in acetonitrile containing PPh$_3$.

The ylides derived from these phosphonium salts (and prepared by treatment with n-BuLi in hexane at −70° C. with exclusion of oxygen) react with aldehydes to give cis-olefins. These cis-olefins are then isomerized by the phosphorus-betaine method of E. Vedejs and P. C. Fuchs (JACS 95 822 (1973)) to give the trans-olefins.

In the case where $Q^2=CH_3$, n is preferably 0. To synthesize these preferred compounds, a carboxylic acid of the formula II' is preferably reacted with 2 equivalents of MeLi to give III', from which a compound of the formula I according to the invention is obtained by the Wittig method:

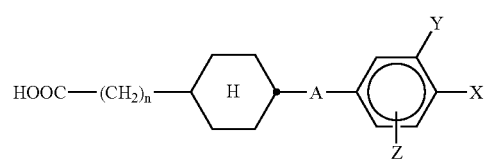

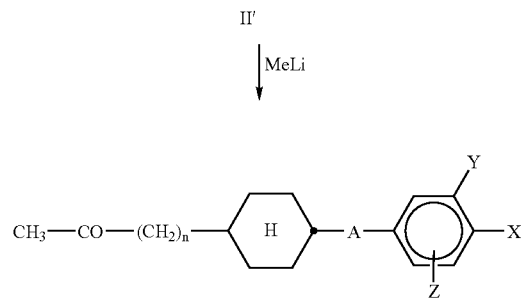

Some of the starting materials of the formula II' and the reactive derivatives thereof are known, and some can be prepared without difficulties from compounds known from the literature by standard methods of organic chemistry. For example, carboxylic acids of the formula II' can be obtained by the following synthetic schemes:

Scheme 1:

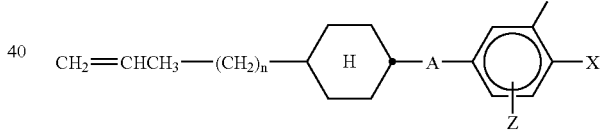

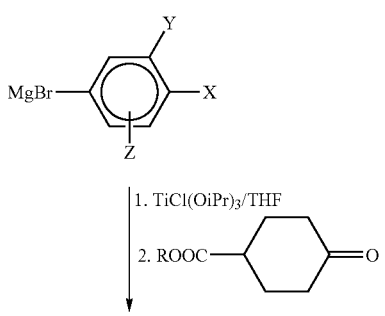

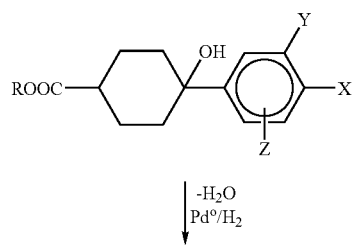
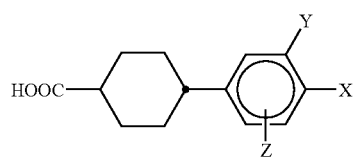
Scheme 2:
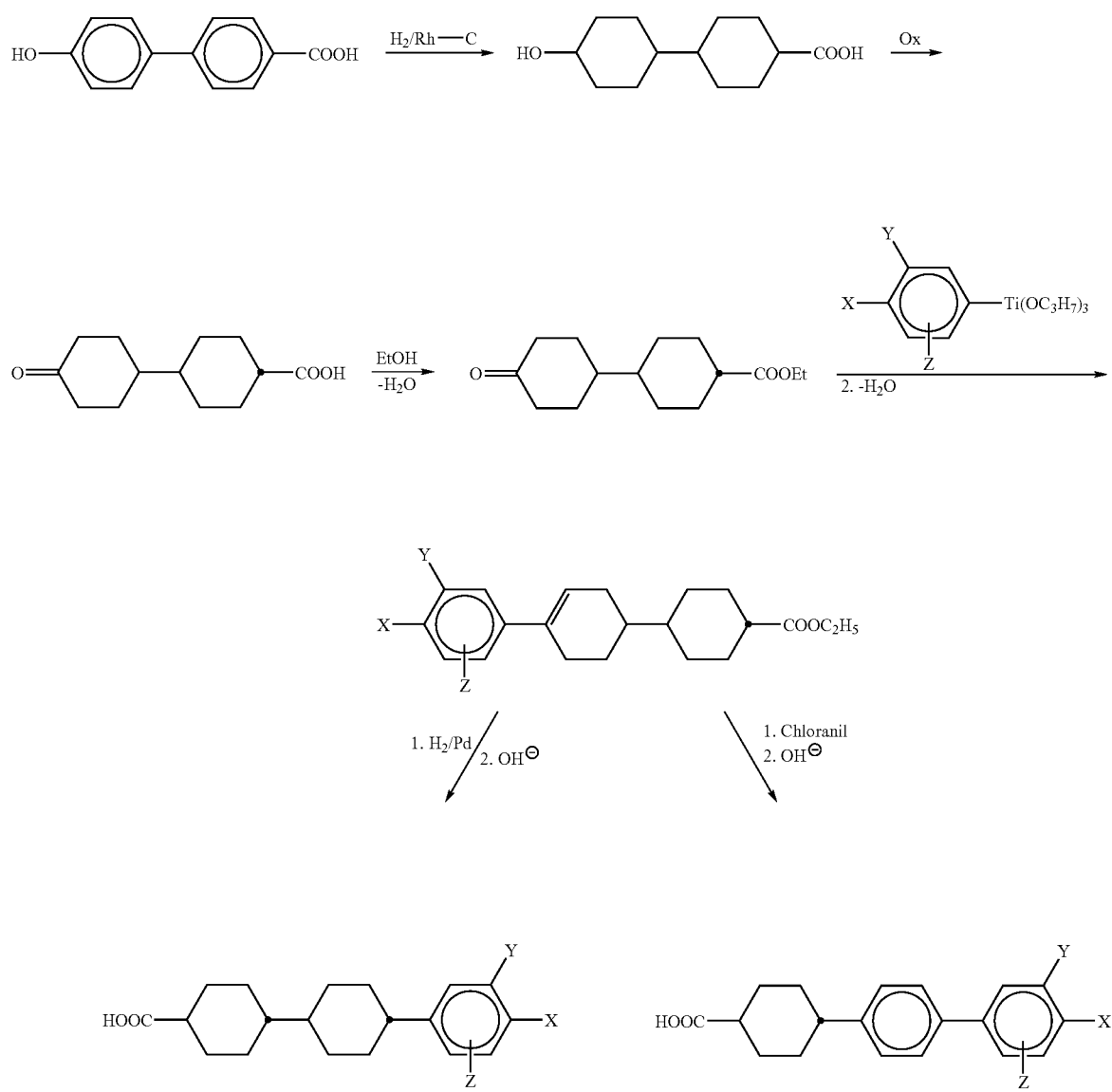

The carboxylic acids mentioned can be converted into the higher homologs (r=1-5) by customary homologization reactions.

In the case where $Q^1=CH_3$, n is preferably 1. To synthesize these preferred compounds, a phosphonium salt of the formula II″ is preferably reacted with acetone by the Wittig method in the presence of a base (for example BuLi) to give a compound according to the invention.

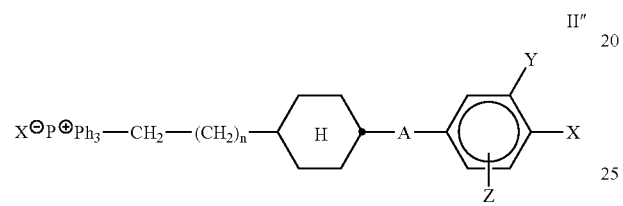

II″

Some of the starting materials of the formula II″ are known, and some can be prepared without difficulties from compounds known from the literature by standard methods of organic chemistry. For example, precursors of the compounds of the formula II″ can be obtained by the following synthetic schemes:

Scheme 3:

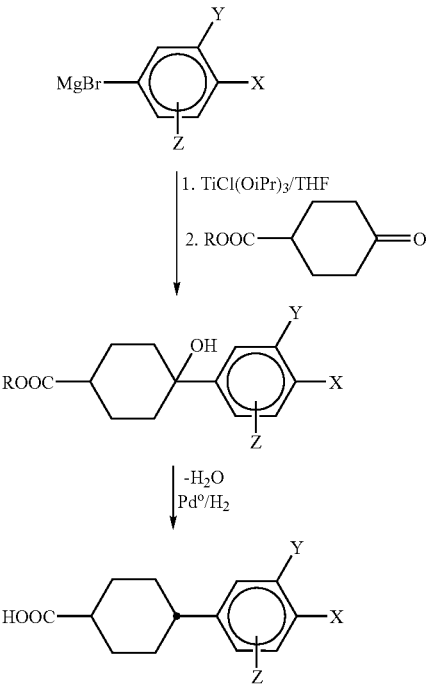

Scheme 4:

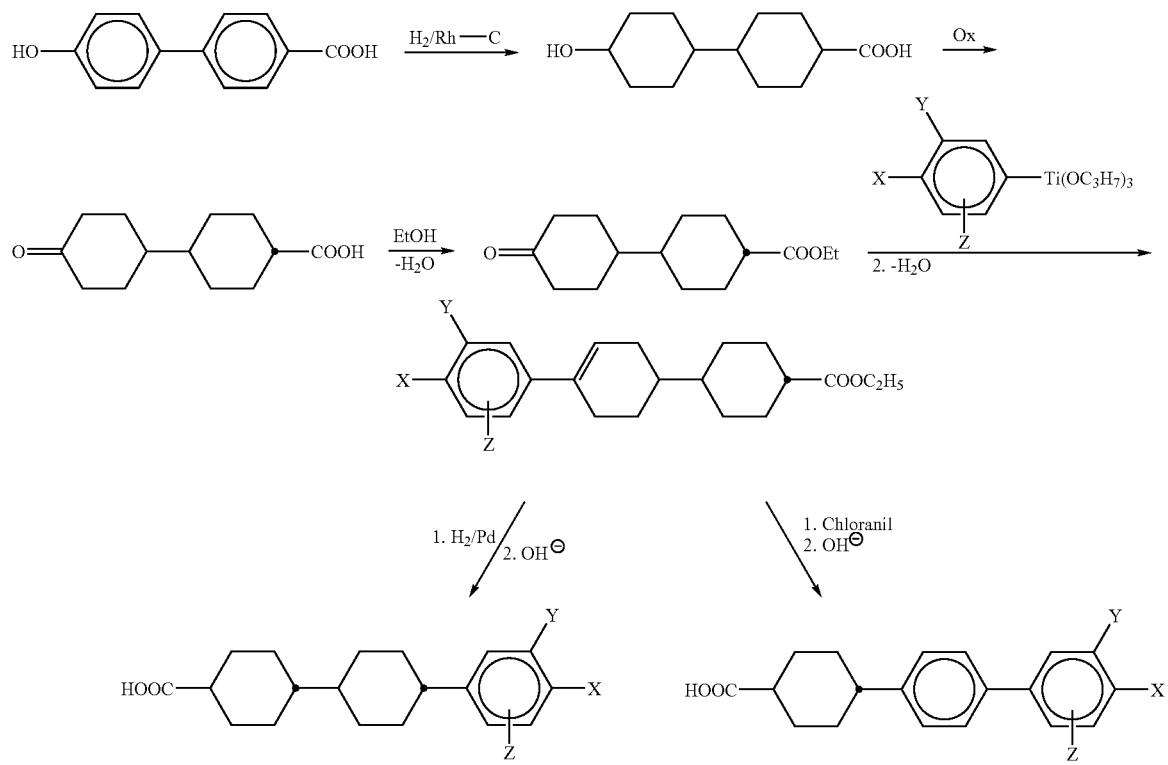

The carboxylic acids mentioned can be converted, if desired, into the higher homologs (r=1 to 5) by customary homologization reactions.

After reduction of the carboxylic acids obtained into the corresponding alcohols and conversion into the bromides or iodides, the phoshonium [sic] salts of the formula II" are obtained therefrom by routine methods.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl) ethanes, 1-cyclohexyl-2-biphenylylethanes, 1-phenyl-2-cyclohexylphenylethanes and tolans. The 1,4-phenylene groups in these compounds may also be fluorinated.

The most important compounds suitable as further constituents of media according to the invention can be characterized by the formulae 1, 2, 3, 4 and 5:

$$R'\text{-L-E-R''} \qquad 1$$

$$R'\text{-L-COO-E-R''} \qquad 2$$

$$R'\text{-L-OOC-E-R''} \qquad 3$$

$$R'\text{-L-CH}_2\text{CH}_2\text{-E-R''} \qquad 4$$

$$R'\text{-L-CC-E-R''} \qquad 5$$

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In the compounds of the subformulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the subformulae 1b, 2b, 3b, 4b and 5b, R" is —CN, —CF$_3$, —OCF$_3$, —OCHF$_2$, F, Cl or —NCS; in this case, R has the meaning given for the compounds of the subformulae 1a to 5a and is preferably alkyl or alkenyl. R" is preferably selected from the group comprising —F, Cl, —CF$_3$, —OCHF$_2$ and —OCF$_3$. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows: Group 1: 20 to 90%, in particular 30 to 90%, Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention.

The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed.

Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In particular, the media according to the invention are suitable for use in MLC displays.

The examples below are intended to illustrate the invention without representing a limitation. mp.=melting point, cp.=clear point. Above and below, percentages are percent by weight; all temperatures are indicated in degrees Celsius. "Customary work-up" means that water is added, the mixture is extracted with methylene chloride, and the organic phase is separated off, dried and evaporated, and the product is purified by crystallization and/or chromatography.

In addition, the abbreviations have the following meanings: C: crystalline-solid state, S: smectic phase (the index characterizes the phase type), N: nematic state, Ch: cholesteric phase, I: isotropic phase. The number between two symbols indicates the conversion temperature in degrees Celsius.

| | |
|---|---|
| DAST | Diethylaminosulfur trifluoride |
| DCC | Dicyclohexylcarbodiimide |
| DDQ | Dichlorodicyanobenzoquinone |
| DIBALH | Diisobutylaluminum hydride |
| DMSO | Dimethyl sulfoxide |
| POT | Potassium tertiary-butanolate |
| THF | Tetrahydrofuran |
| pTSOH | p-Toluenesulfonic acid |

EXAMPLE 1

One equivalent of potassium t-butylate is added to a mixture of trans-4-(3,4-difluorophenyl)cyclohexanecarbaldehyde and propyltriphenylphosphonium bromide in n-butanol, and the mixture is subjected to customary work-up, to give 4-trans-4-(1-butenyl)cyclohexyl-1,2-difluorobenzene.

EXAMPLE 2

A mixture of 2-trans-4-(p-trifluoromethoxyphenyl)cyclohexylethyltriphenylphosphonium iodide and propanal in hexane is treated with butyllithium, and the mixture is subjected to customary work-up. The 4-trans-4-(cis-2-pentenyl)cyclohexyltrifluoromethoxybenzene obtained is epoxidized using m-chloroperbenzoic acid. 4.15 ml of a 1.15 M solution of lithium diphenylphosphide in THF are added at 25° C. to a solution of the epoxide obtained (0.005 mol) in 15 ml of THF with extremely careful exclusion of atmospheric oxygen.

Disappearance of the red color of the phosphide is awaited, and 1.5 equivalents of freshly distilled methyl iodide are then added to the reaction mixture (likewise at 25° C.). After 2 hours, the mixture is subjected to aqueous work-up. The organic phase is separated off, filtered through silica gel and subsequently evaporated. The residue is purified by chromatography and crystallization, to give 4-trans-4-(trans-2-pentenyl)cyclohexyltrifluoromethoxybenzene.

EXAMPLES 3 to 146

The following compounds of the formula I are obtained analogously to Example 1 or 2 from the corresponding aldehydes:

| | n | r | X | Y | Z | A |
|---|---|---|---|---|---|---|
| (3) | 3 | 0 | F | F | H | '—' |
| (4) | 2 | 1 | F | F | H | '—' |
| (5) | 0 | 2 | F | F | H | '—' |
| (6) | 1 | 2 | F | F | H | '—' |
| (7) | 3 | 2 | F | F | H | '—' |
| (8) | 0 | 0 | F | H | H | '—' |
| (9) | 1 | 0 | F | H | H | '—' |
| (10) | 0 | 2 | F | H | H | '—' |
| (11) | 1 | 2 | F | H | H | '—' |
| (12) | 3 | 2 | F | H | H | '—' |
| (13) | 0 | 0 | Cl | H | H | '—' |
| (14) | 1 | 0 | Cl | H | H | '—' |
| (15) | 0 | 2 | Cl | H | H | '—' |
| (16) | 1 | 2 | Cl | H | H | '—' |
| (17) | 3 | 2 | Cl | H | H | '—' |
| (18) | 0 | 0 | Cl | F | H | '—' |
| (19) | 1 | 0 | Cl | F | H | '—' |
| (20) | 0 | 2 | Cl | F | H | '—' |
| (21) | 1 | 2 | Cl | F | H | '—' |
| (22) | 3 | 2 | Cl | H | H | '—' |
| (23) | 0 | 0 | —CF$_3$ | H | H | '—' |
| (24) | 1 | 0 | —CF$_3$ | H | H | '—' |
| (25) | 0 | 2 | —CF$_3$ | H | H | '—' |
| (26) | 1 | 2 | —CF$_3$ | H | H | '—' |
| (27) | 3 | 2 | —CF$_3$ | H | H | '—' |
| (28) | 0 | 0 | —OCF$_3$ | H | H | '—' |
| (29) | 1 | 0 | —OCF$_3$ | H | H | '—' |
| (30) | 0 | 2 | —OCF$_3$ | H | H | '—' |
| (31) | 1 | 2 | —OCF$_3$ | H | H | '—' |
| (32) | 3 | 2 | —OCF$_3$ | H | H | '—' |
| (33) | 0 | 0 | —OCHF$_3$ | H | H | '—' |
| (34) | 1 | 0 | —OCHF$_3$ | H | H | '—' |
| (35) | 0 | 2 | —OCHF$_3$ | H | H | '—' |
| (36) | 1 | 2 | —OCHF$_3$ | H | H | '—' |
| (37) | 3 | 2 | —OCHF$_3$ | H | H | '—' |
| (38) | 0 | 0 | —CN | F | H | '—' |
| (39) | 1 | 0 | —CN | F | H | '—' |
| (40) | 0 | 2 | —CN | F | H | '—' |
| (41) | 1 | 2 | —CN | F | H | '—' |
| (42) | 3 | 2 | —CN | F | H | '—' |
| (43) | 0 | 0 | —CN | F | F$^x$ | '—' |
| (44) | 1 | 0 | —CN | F | F$^x$ | '—' |
| (45) | 0 | 2 | —CN | F | F$^x$ | '—' |
| (46) | 1 | 2 | —CN | F | F$^x$ | '—' |
| (47) | 3 | 2 | —CN | F | F$^x$ | '—' |
| (57) | 3 | 0 | F | F | H | Cyc |
| (58) | 2 | 1 | F | F | H | Cyc |
| (59) | 0 | 2 | F | F | H | Cyc |
| (60) | 1 | 2 | F | F | H | Cyc |
| (61) | 3 | 2 | F | F | H | Cyc |
| (62) | 0 | 0 | F | H | H | Cyc |
| (63) | 1 | 0 | F | H | H | Cyc |
| (64) | 0 | 2 | F | H | H | Cyc |
| (65) | 1 | 2 | F | H | H | Cyc |
| (66) | 3 | 2 | F | H | H | Cyc |
| (67) | 0 | 0 | Cl | H | H | Cyc |
| (68) | 1 | 0 | Cl | H | H | Cyc |
| (69) | 0 | 2 | Cl | H | H | Cyc |
| (70) | 1 | 2 | Cl | H | H | Cyc |
| (71) | 3 | 2 | Cl | H | H | Cyc |
| (72) | 0 | 0 | Cl | F | H | Cyc |
| (73) | 1 | 0 | Cl | F | H | Cyc |
| (74) | 0 | 2 | Cl | F | H | Cyc |
| (75) | 1 | 2 | Cl | F | H | Cyc |
| (76) | 3 | 2 | Cl | F | H | Cyc |
| (77) | 0 | 0 | —CF$_3$ | H | H | Cyc |
| (78) | 1 | 0 | —CF$_3$ | H | H | Cyc |
| (7) | 0 | 2 | —CF$_3$ | H | H | Cyc |
| (80) | 1 | 2 | —CF$_3$ | H | H | Cyc |
| (81) | 3 | 2 | —CF$_3$ | H | H | Cyc |
| (82) | 0 | 0 | —OCF$_3$ | H | H | Cyc |
| (83) | 1 | 0 | —OCF$_3$ | H | H | Cyc |
| (84) | 0 | 2 | —OCF$_3$ | H | H | Cyc |
| (85) | 1 | 2 | —OCF$_3$ | H | H | Cyc |
| (86) | 3 | 2 | —OCF$_3$ | H | H | Cyc |
| (87) | 0 | 0 | —OCHF$_3$ | H | H | Cyc |
| (88) | 1 | 0 | —OCHF$_3$ | H | H | Cyc |
| (89) | 0 | 2 | —OCHF$_2$ | H | H | Cyc |
| (90) | 1 | 2 | —OCHF$_2$ | H | H | Cyc |
| (91) | 3 | 2 | —OCHF$_2$ | H | H | Cyc |
| (92) | 0 | 0 | —CN | F | H | Cyc |
| (93) | 1 | 0 | —CN | F | H | Cyc |
| (94) | 0 | 2 | —CN | F | H | Cyc |
| (95) | 1 | 2 | —CN | F | H | Cyc |
| (96) | 3 | 2 | —CN | F | H | Cyc |
| (97) | 0 | 0 | —CN | F | F$^x$ | Cyc |
| (98) | 1 | 0 | —CN | F | F$^x$ | Cyc |
| (99) | 0 | 2 | —CN | F | F$^x$ | Cyc |
| (100) | 1 | 2 | —CN | F | F$^x$ | Cyc |
| (101) | 3 | 2 | —CN | F | F$^x$ | Cyc |
| (102) | 3 | 0 | F | F | H | Phe |
| (103) | 2 | 1 | F | F | H | Phe |
| (104) | 0 | 2 | F | F | H | Phe |
| (105) | 1 | 2 | F | F | H | Phe |
| (106) | 3 | 2 | F | F | H | Phe |
| (107) | 0 | 0 | F | H | H | Phe |
| (108) | 1 | 0 | F | H | H | Phe |

-continued

| | n | r | X | Y | Z | A |
|---|---|---|---|---|---|---|
| (109) | 0 | 2 | F | H | H | Phe |
| (110) | 1 | 2 | F | H | H | Phe |
| (111) | 3 | 2 | F | H | H | Phe |
| (112) | 0 | 0 | Cl | H | H | Phe |
| (113) | 1 | 0 | Cl | H | H | Phe |
| (114) | 0 | 2 | Cl | H | H | Phe |
| (115) | 1 | 2 | Cl | H | H | Phe |
| (116) | 3 | 2 | Cl | H | H | Phe |
| (117) | 0 | 0 | Cl | F | H | Phe |
| (118) | 1 | 0 | Cl | F | H | Phe |
| (119) | 0 | 2 | Cl | F | H | Phe |
| (120) | 1 | 2 | Cl | F | H | Phe |
| (121) | 3 | 2 | Cl | F | H | Phe |
| (122) | 0 | 0 | —CF$_3$ | H | H | Phe |
| (123) | 1 | 0 | —CF$_3$ | H | H | Phe |
| (124) | 0 | 2 | —CF$_3$ | H | H | Phe |
| (125) | 1 | 2 | —CF$_3$ | H | H | Phe |
| (126) | 3 | 2 | —CF$_3$ | H | H | Phe |
| (127) | 0 | 0 | —OCF$_3$ | H | H | Phe |
| (128) | 1 | 0 | —OCF$_3$ | H | H | Phe |
| (129) | 0 | 2 | —OCF$_3$ | H | H | Phe |
| (130) | 1 | 2 | —OCF$_3$ | H | H | Phe |
| (131) | 3 | 2 | —OCF$_3$ | H | H | Phe |
| (132) | 0 | 0 | —OCHF$_2$ | H | H | Phe |
| (133) | 1 | 0 | —OCHF$_2$ | H | H | Phe |
| (134) | 0 | 2 | —OCHF$_2$ | H | H | Phe |
| (135) | 1 | 2 | —OCHF$_2$ | H | H | Phe |
| (136) | 3 | 2 | —OCHF$_2$ | H | H | Phe |
| (137) | 0 | 0 | —CN | F | H | Phe |
| (138) | 1 | 0 | —CN | F | H | Phe |
| (139) | 0 | 2 | —CN | F | H | Phe |
| (140) | 1 | 2 | —CN | F | H | Phe |
| (141) | 3 | 2 | —CN | F | H | Phe |
| (142) | 0 | 0 | —CN | F | F$^x$ | Phe |
| (143) | 1 | 0 | —CN | F | F$^x$ | Phe |
| (144) | 0 | 2 | —CN | F | F$^x$ | Phe |
| (145) | 1 | 2 | —CN | F | F$^x$ | Phe |
| (146) | 3 | 2 | —CN | F | F$^x$ | Phe |

$^x$Z in the ortho-position to X

EXAMPLE 147

Reaction of methyl 3-[trans-4-(p-fluorophenyl)cyclohexyl]propyl ketone with methylphosphonium iodide and butyllithium by the Wittig method with customary work-up and purification by chromatography gives trans-1-p-fluorophenyl-4-(4-methylpenten-4-yl)cyclohexane.

EXAMPLES 148 TO 249

The following compounds (n=0, $Q^1$=H, $Q^2$=CH$_3$) are obtained analogously to Example 1 from the corresponding aldehydes:

| | r | X | Y | Z | A |
|---|---|---|---|---|---|
| (148) | 0 | F | H | H | '—' |
| (149) | 1 | F | H | H | '—' |
| (150) | 2 | F | H | H | '—' |
| (151) | 4 | F | H | H | '—' |
| (152) | 0 | F | F | H | '—' |
| (153) | 1 | F | F | H | '—' |
| (154) | 2 | F | F | H | '—' |
| (155) | 3 | F | F | H | '—' |
| (156) | 4 | F | F | H | '—' |
| (157) | 5 | F | F | H | '—' |
| (158) | 0 | Cl | H | H | '—' |
| (159) | 1 | Cl | H | H | '—' |
| (160) | 2 | Cl | H | H | '—' |
| (161) | 3 | Cl | H | H | '—' |
| (162) | 4 | Cl | H | H | '—' |
| (163) | 5 | Cl | H | H | '—' |
| (164) | 0 | Cl | F | H | '—' |
| (165) | 1 | Cl | F | H | '—' |
| (166) | 2 | Cl | F | H | '—' |
| (167) | 3 | Cl | F | H | '—' |
| (168) | 4 | Cl | F | H | '—' |
| (169) | 5 | Cl | F | H | '—' |
| (170) | 0 | CF$_3$ | H | H | '—' |
| (171) | 1 | CF$_3$ | H | H | '—' |
| (172) | 2 | CF$_3$ | H | H | '—' |
| (173) | 3 | CF$_3$ | H | H | '—' |
| (174) | 4 | CF$_3$ | H | H | '—' |
| (175) | 5 | CF$_3$ | H | H | '—' |
| (176) | 0 | OCF$_3$ | H | H | '—' |
| (177) | 1 | OCF$_3$ | H | H | '—' |
| (178) | 2 | OCF$_3$ | H | H | '—' |
| (179) | 0 | OCHF$_2$ | H | H | '—' |
| (180) | 1 | OCHF$_2$ | H | H | '—' |
| (181) | 2 | OCHF$_2$ | H | H | '—' |
| (182) | 0 | F | H | H | Cyc |
| (183) | 1 | F | H | H | Cyc |
| (184) | 2 | F | H | H | Cyc |
| (185) | 3 | F | H | H | Cyc |
| (186) | 0 | F | F | H | Cyc |
| (187) | 1 | F | F | H | Cyc |
| (188) | 2 | F | F | H | Cyc |
| (189) | 3 | F | F | H | Cyc |
| (190) | 4 | F | F | H | Cyc |
| (191) | 5 | F | F | H | Cyc |
| (192) | 0 | Cl | H | H | Cyc |
| (193) | 1 | Cl | H | H | Cyc |
| (194) | 2 | Cl | H | H | Cyc |
| (195) | 3 | Cl | H | H | Cyc |
| (196) | 4 | Cl | H | H | Cyc |
| (197) | 5 | Cl | H | H | Cyc |
| (198) | 0 | Cl | F | H | Cyc |
| (199) | 1 | Cl | F | H | Cyc |
| (200) | 2 | Cl | F | H | Cyc |
| (201) | 3 | Cl | F | H | Cyc |
| (202) | 4 | Cl | F | H | Cyc |
| (203) | 5 | Cl | F | H | Cyc |
| (204) | 0 | CF$_3$ | H | H | Cyc |
| (205) | 1 | CF$_3$ | H | H | Cyc |
| (206) | 2 | CF$_3$ | H | H | Cyc |
| (207) | 3 | CF$_3$ | H | H | Cyc |
| (208) | 4 | CF$_3$ | H | H | Cyc |
| (209) | 5 | CF$_3$ | H | H | Cyc |
| (210) | 1 | OCF$_3$ | H | H | Cyc |
| (211) | 2 | OCF$_3$ | H | H | Cyc |
| (212) | 3 | OCF$_3$ | H | H | Cyc |
| (213) | 0 | OCHF$_2$ | H | H | Cyc |
| (214) | 1 | OCHF$_2$ | H | H | Cyc |
| (215) | 2 | OCHF$_2$ | H | H | Cyc |
| (216) | 0 | F | H | H | Phe |
| (217) | 1 | F | H | H | Phe |
| (218) | 2 | F | H | H | Phe |
| (219) | 3 | F | H | H | Phe |
| (220) | 0 | F | F | H | Phe |
| (221) | 1 | F | F | H | Phe |
| (222) | 2 | F | F | H | Phe |
| (223) | 3 | F | F | H | Phe |
| (224) | 4 | F | F | H | Phe |
| (225) | 5 | F | F | H | Phe |
| (226) | 0 | Cl | H | H | Phe |
| (227) | 1 | Cl | H | H | Phe |
| (228) | 2 | Cl | H | H | Phe |
| (229) | 3 | Cl | H | H | Phe |
| (230) | 4 | Cl | H | H | Phe |
| (231) | 5 | Cl | H | H | Phe |
| (232) | 0 | Cl | F | H | Phe |
| (233) | 1 | Cl | F | H | Phe |
| (234) | 2 | Cl | F | H | Phe |
| (235) | 3 | Cl | F | H | Phe |
| (236) | 4 | Cl | F | H | Phe |
| (237) | 5 | Cl | F | H | Phe |

-continued

| | r | X | Y | Z | A |
|---|---|---|---|---|---|
| (238) | 0 | $CF_3$ | H | H | Phe |
| (239) | 1 | $CF_3$ | H | H | Phe |
| (240) | 2 | $CF_3$ | H | H | Phe |
| (241) | 3 | $CF_3$ | H | H | Phe |
| (242) | 4 | $CF_3$ | H | H | Phe |
| (243) | 5 | $CF_3$ | H | H | Phe |
| (244) | 1 | $OCF_3$ | H | H | Phe |
| (245) | 2 | $OCF_3$ | H | H | Phe |
| (246) | 3 | $OCF_3$ | H | H | Phe |
| (247) | 1 | $OCHF_2$ | H | H | Phe |
| (248) | 2 | $OCHF_2$ | H | H | Phe |
| (249) | 3 | $OCHF_2$ | H | H | Phe |

EXAMPLE 250

Reaction of 2-trans-4-(p-fluorophenyl)cyclohexyl]ethylphosphonium [sic] iodide with acetone and butyllithium by the Wittig method with customary work-up and purification by chromatography gives trans-1-p-fluorophenyl-4-(4-methylpenten-3-yl)cyclohexane.

EXAMPLES 251-352

The following compounds (n=1, $Q^1=CH_3$, $Q^2=H$) are obtained analogously to Example 250 from the corresponding aldehydes:

| | r | X | Y | Z | A |
|---|---|---|---|---|---|
| (251) | 0 | F | H | H | '—' |
| (252) | 1 | F | H | H | '—' |
| (253) | 2 | F | H | H | '—' |
| (254) | 4 | F | H | H | '—' |
| (255) | 0 | F | F | H | '—' |
| (256) | 1 | F | F | H | '—' |
| (257) | 2 | F | F | H | '—' |
| (258) | 3 | F | F | H | '—' |
| (259) | 4 | F | F | H | '—' |
| (260) | 5 | F | F | H | '—' |
| (261) | 0 | Cl | H | H | '—' |
| (262) | 1 | Cl | H | H | '—' |
| (263) | 2 | Cl | H | H | '—' |
| (264) | 3 | Cl | H | H | '—' |
| (265) | 4 | Cl | H | H | '—' |
| (266) | 5 | Cl | H | H | '—' |
| (267) | 0 | Cl | F | H | '—' |
| (268) | 1 | Cl | F | H | '—' |
| (269) | 2 | Cl | F | H | '—' |
| (270) | 3 | Cl | F | H | '—' |
| (271) | 4 | Cl | F | H | '—' |
| (272) | 5 | Cl | F | H | '—' |
| (273) | 0 | $CF_3$ | H | H | '—' |
| (274) | 1 | $CF_3$ | H | H | '—' |
| (275) | 2 | $CF_3$ | H | H | '—' |
| (276) | 3 | $CF_3$ | H | H | '—' |
| (277) | 4 | $CF_3$ | H | H | '—' |
| (278) | 5 | $CF_3$ | H | H | '—' |
| (279) | 0 | $OCF_3$ | H | H | '—' |
| (280) | 1 | $OCF_3$ | H | H | '—' |
| (281) | 2 | $OCF_3$ | H | H | '—' |
| (282) | 0 | $OCHF_2$ | H | H | '—' |
| (283) | 1 | $OCHF_2$ | H | H | '—' |
| (284) | 2 | $OCHF_2$ | H | H | '—' |
| (285) | 0 | F | H | H | Cyc |
| (286) | 1 | F | H | H | Cyc |
| (287) | 2 | F | H | H | Cyc |
| (288) | 3 | F | H | H | Cyc |
| (289) | 0 | F | F | H | Cyc |
| (290) | 1 | F | F | H | Cyc |
| (291) | 2 | F | F | H | Cyc |
| (292) | 3 | F | F | H | Cyc |
| (293) | 4 | F | F | H | Cyc |
| (294) | 5 | F | F | H | Cyc |
| (295) | 0 | Cl | H | H | Cyc |
| (296) | 1 | Cl | H | H | Cyc |
| (297) | 2 | Cl | H | H | Cyc |
| (298) | 3 | Cl | H | H | Cyc |
| (299) | 4 | Cl | H | H | Cyc |
| (300) | 5 | Cl | H | H | Cyc |
| (301) | 0 | Cl | F | H | Cyc |
| (302) | 1 | Cl | F | H | Cyc |
| (303) | 2 | Cl | F | H | Cyc |
| (304) | 3 | Cl | F | H | Cyc |
| (305) | 4 | Cl | F | H | Cyc |
| (306) | 5 | Cl | F | H | Cyc |
| (307) | 0 | $CF_3$ | H | H | Cyc |
| (308) | 1 | $CF_3$ | H | H | Cyc |
| (309) | 2 | $CF_3$ | H | H | Cyc |
| (310) | 3 | $CF_3$ | H | H | Cyc |
| (311) | 4 | $CF_3$ | H | H | Cyc |
| (312) | 5 | $CF_3$ | H | H | Cyc |
| (313) | 1 | $OCF_3$ | H | H | Cyc |
| (314) | 2 | $OCF_3$ | H | H | Cyc |
| (315) | 3 | $OCF_3$ | H | H | Cyc |
| (316) | 0 | $OCHF_2$ | H | H | Cyc |
| (317) | 1 | $OCHF_2$ | H | H | Cyc |
| (318) | 2 | $OCHF_2$ | H | H | Cyc |
| (319) | 0 | F | H | H | Phe |
| (320) | 1 | F | H | H | Phe |
| (321) | 2 | F | H | H | Phe |
| (322) | 3 | F | H | H | Phe |
| (323) | 0 | F | F | H | Phe |
| (324) | 1 | F | F | H | Phe |
| (325) | 2 | F | F | H | Phe |
| (326) | 3 | F | F | H | Phe |
| (327) | 4 | F | F | H | Phe |
| (328) | 5 | F | F | H | Phe |
| (329) | 0 | Cl | H | H | Phe |
| (330) | 1 | Cl | H | H | Phe |
| (331) | 2 | Cl | H | H | Phe |
| (332) | 3 | Cl | H | H | Phe |
| (333) | 4 | Cl | H | H | Phe |
| (334) | 5 | Cl | H | H | Phe |
| (335) | 0 | Cl | F | H | Phe |
| (336) | 1 | Cl | F | H | Phe |
| (337) | 2 | Cl | F | H | Phe |
| (338) | 3 | Cl | F | H | Phe |
| (339) | 4 | Cl | F | H | Phe |
| (340) | 5 | Cl | F | H | Phe |
| (341) | 0 | $CF_3$ | H | H | Phe |
| (342) | 1 | $CF_3$ | H | H | Phe |
| (343) | 2 | $CF_3$ | H | H | Phe |
| (344) | 3 | $CF_3$ | H | H | Phe |
| (345) | 4 | $CF_3$ | H | H | Phe |
| (346) | 5 | $CF_3$ | H | H | Phe |
| (347) | 1 | $OCF_3$ | H | H | Phe |
| (348) | 2 | $OCF_3$ | H | H | Phe |
| (349) | 3 | $OCF_3$ | H | H | Phe |
| (350) | 1 | $OCHF_2$ | H | H | Phe |
| (351) | 2 | $OCHF_2$ | H | H | Phe |
| (352) | 3 | $OCHF_2$ | H | H | Phe |

The following are examples of media containing at least one compound of the formula I:

EXAMPLE A

A mixture comprising

7% of p-(trans-4-propylcyclohexyl)benzonitrile,
5% of 4-[trans-4-(trans-2-pentenyl)cyclohexyl]trifluoromethoxybenzene,
24% of p-(trans-4-pentylcyclohexyl)fluorobenzene,
14% of p-(trans-4-heptylcyclohexyl)fluorobenzene, 15% of 2-[trans-4-(3,4-difluorophenyl)cyclohexyl]-5-butyl-1,3-dioxane,
18% of 2-[trans-4-(p-fluorophenyl)cyclohexyl]-5-ethyl-1,3-dioxane, and
17% of 2-[trans-4-(p-fluorophenyl)cyclohexyl]-5-propyl-1,3-dioxane has a high electrical resistance.

The invention claimed is:

1. A phenylcyclohexane of formula I

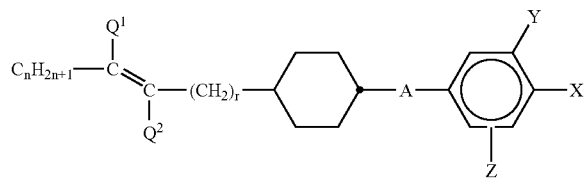

in which n is 0 to 7, $Q^1$ and $Q^2$ are H, or one of $Q^1$ and $Q^2$ is alternatively $CH_3$, r is 0, or 2, A is a trans 1,4 cyclohexylene, 1,4 phenylene, 3-fluoro-1,4 phenylene or a single bond, X is F, Cl, $—CF_3$, $—CN$, $—OCF_3$, or $—OCHF_2$, and Y and Z are both F.

2. A phenylcyclohexane according to claim 1, wherein X is F, Cl, $—CF_3$ or $—OCF_3$.

3. A liquid-crystalline medium having at least two liquid-crystalline components, wherein at least one component is a phenylcyclohexane of formula I according to claim 1.

4. An electrooptical display based on a liquid-crystal cell, wherein the liquid-crystal cell contains a medium according to claim 3.

5. A phenylcyclohexane according to claim 1, wherein r is 0.

6. A phenylcyclohexane according to claim 1, wherein r is 2.

7. A liquid crystalline medium having at least two liquid crystalline components, wherein at least one component is a phenylcyclohexane of the formula I according to claim 5.

8. An electrooptical display based on a liquid-crystal cell, wherein the liquid-crystal cell contains a medium according to claim 7.

9. A liquid crystalline medium having at least two liquid crystalline components, wherein at least one component is a phenylcyclohexane of the formula I according to claim 6.

10. An electrooptical display based on a liquid-crystal cell, wherein the liquid-crystal cell contains a medium according to claim 9.

11. A phenylcyclohexane according to claim 1, wherein X is CN, r is 0, A is a single bond, and $Q^1$ and $Q^2$ are both H.

12. A phenylcyclohexane according to claim 11 wherein n is 0.

13. A phenylcyclohexane according to claim 11 wherein n is 1.

14. A liquid crystalline medium having at least two components, wherein at least one component is a phenylcyclohexane of the formula I according to claim 11.

15. A electrooptical display based on a liquid crystal cell containing a medium according to claim 14.

16. A liquid crystalline medium having at least two components, wherein at least one component is a phenylcyclohexane of the formula I according to claim 12.

17. A electrooptical display based on a liquid crystal cell containing a medium according to claim 16.

18. A liquid crystalline medium heaving at least two components, wherein at least one component is a phenylcyclohexane according to claim 13.

19. A electrooptical display based on a liquid crystal cell containing a medium according to claim 18.

* * * * *